United States Patent
Gibson et al.

(10) Patent No.: US 9,516,893 B2
(45) Date of Patent: Dec. 13, 2016

(54) USE OF TRYPTOPHAN RICH PROTEIN HYDROLYSATES

(71) Applicant: DSM IP ASSETS B.V., Heerlen (NL)

(72) Inventors: Leigh Gibson, Basel (CH); Regina Goralczyk, Basel (CH); Hasan Mohajeri, Basel (CH); Jonas Wittwer Schegg, Basel (CH); Nicolle Goetz, Basel (CH); Christina Kalarickal, Basel (CH); Simone Koenig-Grillo, Basel (CH); Marja Kanning, Basel (CH); Damiet Josephina Petronella Cunera Koenders, Basel (CH); Kathleen Simons, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/404,878

(22) PCT Filed: Oct. 30, 2013

(86) PCT No.: PCT/IB2013/059789
§ 371 (c)(1),
(2) Date: Dec. 1, 2014

(87) PCT Pub. No.: WO2014/068499
PCT Pub. Date: May 8, 2014

(65) Prior Publication Data
US 2015/0296853 A1    Oct. 22, 2015

Related U.S. Application Data

(60) Provisional application No. 61/721,525, filed on Nov. 2, 2012, provisional application No. 61/721,543, filed on Nov. 2, 2012, provisional application No. 61/721,524, filed on Nov. 2, 2012, provisional application No. 61/721,526, filed on Nov. 2, 2012, provisional application No. 61/721,529, filed on Nov. 2, 2012, provisional application No. 61/721,581, filed on Nov. 2, 2012.

(51) Int. Cl.
| | |
|---|---|
| A23L 1/30 | (2006.01) |
| A23L 1/305 | (2006.01) |
| A23L 2/66 | (2006.01) |
| A61K 9/00 | (2006.01) |
| A61K 38/47 | (2006.01) |
| A61K 47/12 | (2006.01) |
| A61K 38/00 | (2006.01) |

(52) U.S. Cl.
CPC ............ *A23L 1/3051* (2013.01); *A23K 20/147* (2016.05); *A23L 1/3053* (2013.01); *A23L 2/66* (2013.01); *A61K 9/0095* (2013.01); *A61K 38/47* (2013.01); *A61K 47/12* (2013.01); *A23V 2002/00* (2013.01); *A61K 38/00* (2013.01); *C12Y 302/01017* (2013.01)

(58) Field of Classification Search
CPC ..................................................... A23L 1/3051
See application file for complete search history.

(56) References Cited

U.S. PATENT DOCUMENTS

| | | |
|---|---|---|
| 2009/0269443 A1 | 10/2009 | Van Beckhoven et al. |
| 2011/0086803 A1 | 4/2011 | De Roos et al. |

FOREIGN PATENT DOCUMENTS

| | | | |
|---|---|---|---|
| DE | 10 2005 00624 | 8/2006 | |
| JP | 2004-536030 | 12/2004 | |
| JP | 2011-523457 | 8/2011 | |
| WO | WO 01/54681 | 8/2001 | |
| WO | WO 2008/052995 | * 5/2008 | ............. C12P 21/06 |
| WO | WO 2009/133055 | 11/2009 | |

OTHER PUBLICATIONS

International Search Report for PCT/IB2013/059789 mailed Jan. 27, 2014.
Written Opinion of the International Searching Authority for PCT/IB2013/059789 mailed Jan. 27, 2014.
JP Office Action of Patent Application No. P2015-522248 dated Jan. 5, 2016.
Gibson et. al, "Effects of acute treatment with a tryptophan-rich protein hydrolysate on plasma amino acids, mood and emotional functioning in older women", Psychopharmacology (2014) 231:4595-4610.

\* cited by examiner

*Primary Examiner* — Amber D Steele
(74) *Attorney, Agent, or Firm* — Nixon & Vanderhye P.C.

(57) ABSTRACT

This invention relates to a method of increasing a feeling of a) energy or b) cognitive functions, selected from the group consisting of: sustained attention, faster reaction times, and information processing; or c) quality of sleep; or d) feelings of well-being and happiness in a healthy adult using a dosage form comprising a low dose of a Trp-containing di- and/or tri-peptide mixture characterized in that the peptide composition is an egg lysozyme hydrolysate with a Trp/L!MAA ratio greater than 0.15 and which provides IQ-to 100 mg Trp per dose. This dosage form can be administered acutely or can be administered multiple times per day for an extended period of time.

22 Claims, 6 Drawing Sheets

A

B

C

D

USE OF TRYPTOPHAN RICH PROTEIN HYDROLYSATES

Figure 1:
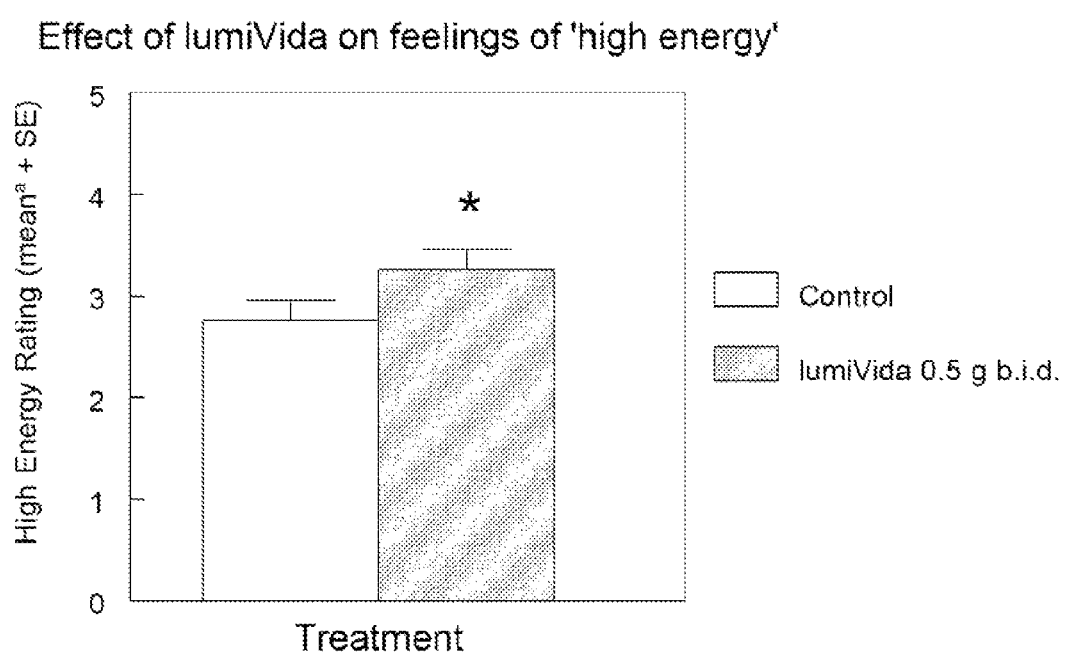

This application is the U.S. national phase of International Application No. PCT/IB2013/059789 filed 30 Oct. 2013 which designated the U.S. and claims the benefit of U.S. Provisional Application No. 61/721,525, filed 2 Nov. 2012, U.S. Provisional Application No. 61/721,543, filed 2 Nov. 2012, U.S. Provisional Application No. 61/721,524, filed 2 Nov. 2012, U.S. Provisional Application No. 61/721,526, filed 2 Nov. 2012, U.S. Provisional Application No. 61/721,529 filed 2 Nov. 2012, and U.S. Provisional Application No. 61/721,581, filed 2 Nov. 2012, the entire contents of each of which are hereby incorporated by reference.

DESCRIPTION OF THE INVENTION

This invention relates to use of tryptophan (Trp)-rich peptides as a food additive or nutritional supplement by a consumer in order to enhance the consumer's feeling of high energy and to promote various cognitive functions, particularly faster reaction times and sustained attention. Sleep quality was also influenced positively. It also helps impart a feeling of well-being and happiness. The dosage used is lower than that used with previous formulations containing Trp-containing protein hydrolysates. Dosing be acute or sustained for a chronic time period. It also relates to formulations of the trp-containing protein hydrolysate, including beverages, sorbets, and nutritional gels.

BACKGROUND OF THE INVENTION

In recent years, a method has been developed to enhance tryptophan "Trp" availability to brain, and so potentially serotonin function, by administering TRP-rich dietary proteins/hydrolysates. These include the whey protein alpha-lactalbumin, and a casein hydrolysate. Since the Trp present in these proteins/hydrolysates competes with Large Neutral Amino Acids (LNAAs which are tyrosine, phenylalanine, leucine, isoleucine and valine) for transport across the blood-brain barrier, a high Trp/LNAA ratio is desired, and this ratio is difficult to achieve with these protein/hydrolysates.

DSM has developed a hen egg white lysozyme hydrolysate formulation that contains fewer competing LNAAs, and is sold under the trademark lumiVida™. LumiVida™ has recently been shown to be more effective in raising plasma Trp/LNAA ratios than either alpha-lactalbumin or L-Trp alone and 4 g lumiVida™ was still able to raise Trp/LNAA ratio when ingested together with milk protein. This hydrolysate has been described in WO 2008/052995, which is hereby incorporated by reference.

Typical dosages which are used in WO 2008/052995 are quite large (10 grams hydrolysate per liter liquid; 14 grams per 300 ml drink) as this appears to be necessary for a significant increase of serum Trp/LNAA ratios, and ultimately increase the Trp availability to the brain. However, the peptides are rather bitter tasting. It would be desirable to have a formulation which was pleasant tasting and also provides enough Trp to the brain as to be effective.

DETAILED DESCRIPTION OF THE INVENTION

It has been surprisingly found, in accordance with this invention that administration of Trp in the form of Trp-rich peptides from a hen's egg lysozyme hydrolysis ("Trp-containing protein hydrolysate") at a low doses can provide enough Trp to the brain so that it is effective. This has two advantages over the prior art higher dose:
1) it can be administered in a low dose pleasantly tasting formulation, and
2) surprisingly, provide a positive feeling of increased energy when used in a low-dosage form when administered acutely, i.e. after only one administration. In addition, the feeling may also be achieved when the Trp-containing protein hydrolysate is administered chronically, i.e. over a period of time.

Accordingly this invention relates to a method of increasing a feeling of energy in a healthy adult comprising administering at least one and preferably a plurality of dosages per day comprising a low dose of a Trp-containing di- and/or tri-peptide mixture characterized in that the peptide composition is a hen's egg lysozyme hydrolysate with a Trp/LNAA ratio greater than 0.15, preferably 0.18 to 0.23; and which provides 25-50 mg Trp per dose, and preferably 25-35 mg Trp per dose. In one preferred embodiment, 500 mg of hydrolysate contains 25-32 mg Trp per dose.

In one embodiment, the dosage may be administered acutely, i.e. the effects are observed regardless of the Trp/LNAA ratio is prior to administration.

This dosage form may also be administered multiple times per day for an extended period of time, such that the person receives 10-100 mg Trp per day, preferably 25-70 mg Trp per day. In one preferred embodiment, the person receives 1 gram of hydrolysate per day, which contains a total of 62-64 mg Trp. In another preferred embodiment, the person receives 0.5 grams of Trp-hydrolysate per day, which contains a total of 20-26 mg Trp.

Preferably the low-dose protein hydrolysate is consumed once per day to achieve acute effects. In another preferred embodiment the protein hydrolysate is consumed 2× per day, with an interval of at least 6 hours between doses, and preferably no more than 18 hours between doses. In more preferred embodiments, the doses are consumed at approximately 12 hour intervals, such as early morning and early evening. Additional dosings per day may also be consumed if desired, such as 2-4 grams Trp-containing protein hydrolysate per day, and these dosings may be seen to have additional benefits. Dosings of greater than 10 grams Trp-containing protein hydrolysate per day are not part of this invention. Thus the dosings of this invention, for a healthy adult wishing to improve energy is enough Trp-containing protein hydrolysate to provide at least 10 mg but less than 400 mg Trp per day, preferably at least 25 mg, but less than 350 mg Trp per day.

In some aspects of this invention the amount of Trp-containing protein hydrolysate which delivers the desired amounts of Trp will be 1000 mg/day, i.e. each dose contains 500 mg Trp-containing protein hydrolysate. In another aspect the amount of Trp-containing protein hydrolysate is 400-600 mg delivered twice per day, or 800-1200 mg per day. It is also in the scope of this invention to administer somewhat larger doses of Trp-containing protein hydrolysate so that the daily dosage exceeds 1000 mg/day, but is less than 10 grams per day. Additional other doses of Trp-hydrolysate are amounts up to 2 grams but less than 4 grams per day (i.e. 1000 mg delivered 2× per day, and 2000 mg delivered 2× per day).

Well-being

It has also been surprisingly found, in accordance with this invention that administration of Trp-containing protein at a low doses can surprisingly, provide an a) increase in certain cognitive functions, especially sustained attention and faster reaction times, and information processing; and b) benefit to quality of sleep, and c) increase in perceptions of well-being and happiness.

Accordingly this invention relates to a method of increasing a) certain cognitive functions, especially sustained attention and faster reaction times, and information processing;

b) quality of sleep; or c) feelings of well being and happiness in a healthy adult comprising administering a at least one and preferably a plurality of dosages per day comprising a low dose of a Trp-containing di- and/or tri-peptide mixture characterized in that the peptide composition is a hen's egg lysozyme hydrolysate with a Trp/LNAA ratio greater than 0.15, preferably 0.18 to 0.23; and which provides 25-50 mg Trp per dose, and preferably 25-35 mg Trp per dose. In one preferred embodiment, 500 mg of hydrolysate contains 25-32 mg Trp per dose.

In one embodiment, the dosage may be administered acutely, i.e. the effects are observed regardless of the Trp/LNAA ratio is prior to administration.

This dosage form may also be administered multiple times per day for an extended period of time, such that the person receives 10-100 mg Trp per day, preferably 25-70 mg Trp per day. In one preferred embodiment, the person receives 1 gram of hydrolysate per day, which contains a total of 62-64 mg Trp. In another preferred embodiment, the person receives 0.5 grams of Trp-hydrolysate per day, which contains a total of 20-26 mg Trp.

Preferably the low-dose protein hydrolysate is consumed once per day to achieve acute effects. In another preferred embodiment the protein hydrolysate is consumed 2× per day, with an interval of at least 6 hours between doses, and preferably no more than 18 hours between doses. In more preferred embodiments, the doses are consumed at approximately 12 hour intervals, such as early morning and early evening. Additional dosings per day may also be consumed if desired, such as 2-4 grams Trp-containing protein hydrolysate per day, and these dosings may be seen to have additional benefits. Dosings of greater than 10 grams Trp-containing protein hydrolysate per day are not part of this invention.

Thus the low dosings of this invention, are sufficient for a healthy adult wishing to increase a) certain cognitive functions, especially sustained attention and faster reaction times, and information processing; or b) benefit to quality of sleep; or c) feelings of well-being and happiness.

In some aspects of this invention the amount of Trp-containing protein hydrolysate which delivers the desired amounts of Trp will be 1000 mg/day, i.e. each dose contains 500 mg Trp-containing protein hydrolysate. In another aspect the amount of Trp-containing protein hydrolysate is 400-600 mg delivered twice per day, or 800-1200 mg per day. It is also in the scope of this invention to administer somewhat larger doses of Trp-containing protein hydrolysate so that the daily dosage exceeds 1000 mg/day, but is less than 10 grams per day. Additional other doses of Trp-hydrolysate are amounts up to 2 grams but less than 4 grams per day (i.e. 1000 mg delivered 2× per day, and 2000 mg delivered 2× per day).

Another aspect of this invention is a convenient to use chronic dosage kit comprising multiple single dose units of a Trp-containing protein hydrolysate with a Trp/LNAA ratio of greater than 0.15, preferably 0.18 to 0.23, and providing 20-50 mg Trp per dose, or 50-100 mg Trp per day. Also included in the kit are the following preferable items: A container for storing the dosage forms, information regarding how the dosages are to be used.

This invention also relates to the use of a low dose of Trp-hydrolysate as described above to make a composition which imparts a feeling in a consumer which is selected from the group consisting of:

a) an increase in certain cognitive functions, especially sustained attention and faster reaction times, and information processing; or b) increased quality of sleep;

c) increased feelings of well-being or happiness

It also relates to the use of a low dose of Trp-hydrolysate as described to make a medicament, food supplement, or food which imparts one or more of the aforementioned benefits.

A further aspect of this invention is a composition comprising 400-600 mg Trp-containing protein hydrolysate, as described above. Another aspect of this invention is a pharmaceutical, nutraceutical or food supplement where the sole active ingredient which imparts a feeling of high energy is Trp-containing protein hydrolysate. Another aspect of this invention is a composition comprising at least 400 mg but less than 4000 mg of Trp-containing protein hydrolysate. Yet another aspect of this invention is a composition comprising at least 400 mg but less than 2000 mg Trp-containing protein hydrolysate.

Beverages

It has also been found in accordance with this invention that powdered hen egg white lysozyme hydrolysate formulations which are lower in dosage than previous hydrolysate formulations can be used to make instant beverages, shots, still drinks, and carbonated drinks which are organoleptically appealing as well as bioavailable. Accordingly one aspect of this invention relates to a method of increasing a) a feeling of energy in a healthy adult;

b) certain cognitive functions, especially sustained attention and faster reaction times, and information processing;

c) quality of sleep; or d) feelings of well-being or happiness comprising administering at least one and preferably a plurality of beverages per day comprising a low dose of a Trp-containing hydrolysate characterized in that the peptide composition is a hen's egg lysozyme hydrolysate with a Trp/LNAA ratio greater than 0.15, preferably 0.18 to 0.23, and which provides 25-50 mg Trp per dose, and preferably 25-35 mg Trp per dose. In one preferred embodiment, 500 mg of hydrolysate contains 25-32 mg Trp per dose.

In one embodiment, the beverage may be administered acutely, i.e. the effects are observed regardless of the Trp/LNAA ratio is prior to administration.

This beverage may also be administered multiple times per day for an extended period of time, such that the person receives 10-100 mg Trp per day, preferably 25-70 mg Trp per day. In one preferred embodiment, the beverage comprises 1 gram of hydrolysate per day, which contains a total of 62-64 mg Trp. In another preferred embodiment, the beverage contains 0.5 grams of Trp-hydrolysate per day, which contains a total of 20-26 mg Trp.

Preferably the low-dose protein hydrolysate beverage is consumed once per day to achieve acute effects. In another preferred embodiment, the beverage is consumed 2× per day, with an interval of at least 6 hours between doses, and preferably no more than 18 hours between doses. In more preferred embodiments, the beverages are consumed at approximately 12 hour intervals, such as morning and early evening. Additional beverages may also be consumed if desired, such as 2-4 grams Trp-containing protein hydrolysate per day, and these dosings may be seen to have additional benefits. Dosings of greater than 10 grams Trp-containing protein hydrolysate per day are not part of this invention. Thus the dosings of this invention, for a healthy adult wishing to improve energy is enough Trp-containing protein hydrolysate beverage to provide at least 10 mg but less than 400 mg grams Trp per day, preferably at least 25 mg, but less than 350 mg Trp per day.

Sorbet

This invention also relates to a method of increasing
  a) a feeling of energy in a healthy adult;
  b) certain cognitive functions, especially sustained attention and faster reaction times, and information processing;
  c) quality of sleep; or
  d) feelings of well-being or happiness
comprising administering at least one and preferably a plurality of dosages per day of a sorbet comprising a low dose of a Trp-containing protein hydrolysate characterized in that the peptide composition is a hen's egg lysozyme hydrolysate with a Trp/LNAA ratio greater than 0.15, preferably 0.18 to 0.23, and which provides 10-70 mg Trp per dose, preferably 20-70 mg, and more preferably 25-60 mg Trp per dose. In one preferred embodiment, 500 mg of Trp-containing protein hydrolysate contains 20-32 mg Trp per dose.

In one embodiment the sorbet is taken in a single dose (acutely). The effects of the low dosage may be observed regardless of the Trp/LNAA ratio is prior to administration.

The sorbet can be administered multiple times per day for an extended period of time, such that the person receives 10-100 mg Trp per day, preferably 25-70 mg Trp per day. In one preferred embodiment, the person receives sorbet having 1 gram of Trp-containing hydrolysate per day, which contains a total of 52-64 mg Trp. In another preferred embodiment, the person receives sorbet having 0.5 grams of Trp-containing protein hydrolysate per day, which contains a total of 20-30 mg Trp.

To achieve the acute effect, the sorbet can be consumed once per day. A preferred dose in sorbet containing 500 mg Trp-containing protein hydrolysate.

In another preferred embodiment the sorbet with the Trp-containing protein hydrolysate is consumed 2× per day, with an interval of at least 6 hours between doses, and preferably no more than 18 hours between doses. In more preferred embodiments, the doses are consumed at approximately 12 hour intervals, such as early morning and early evening. Additional dosings per day may also be consumed if desired, such as 2-4 grams Trp-containing protein hydrolysate per day, and these dosings may be seen to have additional benefits. Dosings of greater than 10 grams Trp-containing protein hydrolysate per day are not part of this invention. Thus the dosings of this invention, for a healthy adult wishing to improve energy, is a sorbet containing enough Trp-containing protein hydrolysate to provide at least 10 mg but less than 800 mg Trp per day, preferably at least 25 mg, but less than 500 mg Trp per day.

In some aspects of this invention the amount of Trp-containing protein hydrolysate present in the sorbet will be 1000 mg/day, i.e. each dose contains 500 mg Trp-containing protein hydrolysate. In another aspect the amount of Trp-containing protein hydrolysate in the sorbet is 400-600 mg delivered twice per day, or 800-1200 mg per day.

While a single serving of sorbet preferably contains 0.5 grams of Trp-containing protein hydrolysate, it is also in the scope of this invention to administer somewhat larger doses of Trp-containing protein hydrolysate in the sorbet so that the daily dosage exceeds 1000 mg/day, but is less than 10 grams per day. Additional other doses of Trp-containing protein hydrolysate are amounts of greater than 0.5 grams to 2 grams per day; from 0.5 grams to less than 4 grams per day (i.e. 1000 mg delivered 2× per day, and 2000 mg delivered 2× per day) present in a sorbet.

Preferable dosings of Trp-containing protein hydrolysate include 1 gram per serving of sorbet, 1.5 grams per serving of sorbet, 2 grams per serving of sorbet, and 4 grams per serving of sorbet. In these forms, a single serving can meet a daily dosing requirement of at least 1 gram. These servings can substitute or be used in addition to smaller (500 mg) doses to make up a chronic dosing regime.

Another aspect of this invention is a convenient to use chronic dosage kit comprising multiple single dose units of an egg lysozyme hydrolysate with a Trp/LNAA ratio of greater than 0.15, preferably 0.18 to 0.23 and providing 10-70 mg Trp per dose, or 20-100 mg Trp per day, wherein at least one of the dosings is a sorbet form. Also included in the kit are the following preferable items: A container for storing the dosage forms, information regarding how the dosages are to be used.

Nutritional Gel

It has also been surprisingly found, in accordance with this invention that administration of Trp in the form of a nutritional gel containing Trp-rich peptides from a hen's egg lysozyme hydrolysis ("Trp-hydrolysate") at a low doses can provide enough Trp to the brain so that it is effective.

Accordingly this invention relates to a method of increasing

Accordingly one aspect of this invention relates to a method of increasing
  a) a feeling of energy;
  b) certain cognitive functions, especially sustained attention and faster reaction times, and information processing;
  c) quality of sleep; or
  d) feelings of well-being or happiness
in a healthy adult comprising administering at least one and preferably a plurality of dosages per day of a nutritional gel comprising a low dose of a Trp-containing di- and/or tri-peptide mixture characterized in that the peptide composition is a hen's egg lysozyme hydrolysate with a Trp/LNAA ratio greater than 0.15, preferably 0.18 to 0.23 and which provides 10-70 mg Trp per dose, preferably 20-70 mg Trp per dose, and more preferably 25-60 mg Trp per dose. In one preferred embodiment, the nutritional gel has 500 mg of Trp-containing protein hydrolysate which contains 25-32 mg Trp per dose.

In one embodiment, the nutritional gel dosage may be administered acutely, i.e. the effects are observed regardless of the Trp/LNAA ratio is prior to administration.

The nutritional gel can also be administered multiple times per day for an extended period of time, such that the person receives 10-100 mg Trp per day, preferably 25-70 mg Trp per day. In one preferred embodiment, the person receives 1 gram of Trp-containing protein hydrolysate per day in a nutritional gel, which contains a total of 52-64 mg Trp. In another preferred embodiment, the person receives 0.5 grams of Trp-hydrolysate per day in the nutritional gel, which contains a total of 20-30 mg Trp.

Preferably the low-dose protein hydrolysate in the form of a nutritional gel is consumed once per day to achieve acute effects. In another preferred embodiment the low-dose hydrolysate nutritional gel may also be consumed 2× per day, with an interval of at least 6 hours between doses, and preferably no more than 18 hours between doses. In more preferred embodiments, the doses are consumed at approximately 12 hour intervals, such as early morning and early evening. Additional dosings per day may also be consumed if desired, such as 2-4 grams hydrolysate per day, and these dosings may be seen to have additional benefits. Gels containing doses of greater than 10 grams Trp-containing protein hydrolysate are not part of this invention. Thus, for a healthy adult wishing to improve energy, a gel containing enough Trp-containing protein hydrolysate to provide at least 25 mg but less than 800 mg Trp per day, preferably at least 30 mg, but less than 500 mg Trp per day can be consumed.

In another aspect of this invention, the nutritional gel contains Trp-containing protein hydrolysate at a somewhat higher dosage, i.e. from greater than 500 mg per serving to 4 grams per serving. Preferable dosings include 1 gram per serving, 1.5 grams per serving, 2 grams per serving, and 4 grams per serving. In these forms, a single serving can meet a daily dosing requirement of at least 1 gram. These servings can substitute or be used in addition to smaller (500 mg) doses to make up a chronic dosing regime.

Another aspect of this invention is a convenient to use chronic dosage kit comprising multiple single dose units of an egg lysozyme hydrolysate with a Trp/LNAA ratio of greater than 0.15, preferably 0.18 to 0.23 and providing 20-70 mg Trp per dose, or 40-140 mg Trp per day, wherein at least one of the dosings is a nutritional gel form. Also included in the kit are the following preferable items: A container for storing the dosage forms, information regarding how the dosages are to be used.

Another aspect of this invention is a convenient to use chronic dosage kit comprising multiple single dose units of an egg lysozyme hydrolysate with a Trp/LNAA ratio of greater than 0.15, preferably 0.18 to 0.23 and providing 20-50 mg Trp per dose, or 50-100 mg Trp per day. Also included in the kit are the following preferable items: A container for storing the dosage forms, information regarding how the dosages are to be used.

This invention also relates to the use of a low dose of Trp-hydrolysate as described above to make a composition which imparts:
a) a feeling of increased energy;
b) increased certain cognitive functions, especially sustained attention and faster reaction times, and information processing;
c) increased quality of sleep; or
d) increased feelings of well-being or happiness
in the consumer, preferably a healthy adult. It also relates to the use of a low dose of Trp-hydrolysate as described to make a medicament, food supplement, or food which imparts a feeling of high energy in the consumer.

A further aspect of this invention is a composition comprising 400-600 mg Trp-containing protein hydrolysate, as described above. Another aspect of this invention is a pharmaceutical, nutraceutical or food supplement where the sole active ingredient which imparts a feeling selected from the group consisting of: of high energy; increased cognitive functions, especially sustained attention and faster reaction times, and information processing; quality of sleep; and feelings of well-being or happiness; is Trp-containing protein hydrolysate. Another aspect of this invention is a composition comprising at least 400 mg but less than 4000 mg of Trp-containing protein hydrolysate. Yet another aspect of this invention is a composition comprising at least 400 mg but less than 2000 mg Trp-containing protein hydrolysate.

FIGURES

FIG. 1 is a graph showing the effects of treatments on overall ratings for 'high energy' on the final test day. Chronic lumiVida™ (0.5 g b.i.d.) treatment significantly enhanced high energy levels compared to Control. $^a$Means adjusted for baseline levels.

Figure 2:
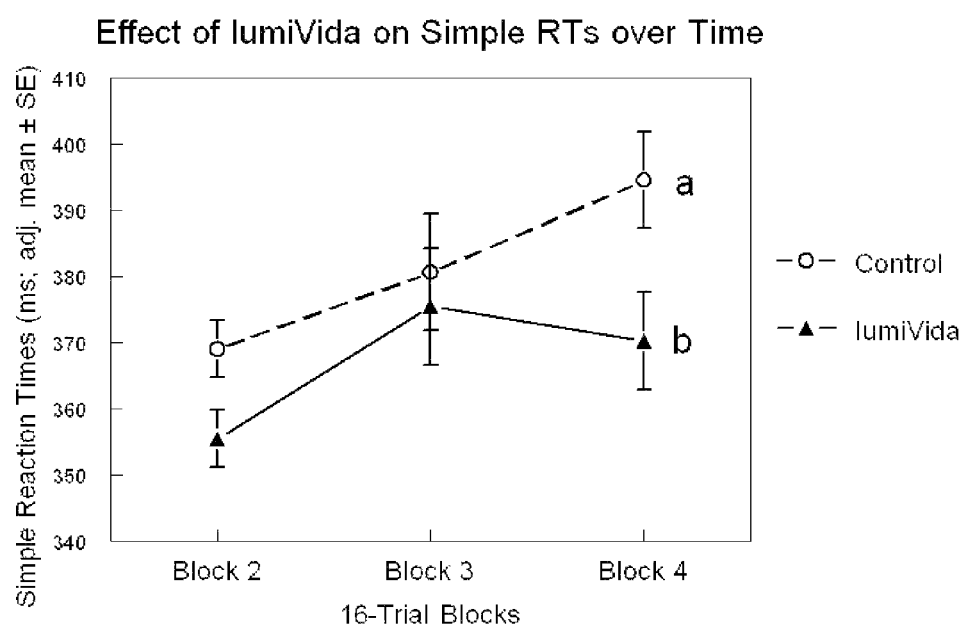

FIG. 2: Effect of lumiVida™ on the change in simple reaction times over three trial blocks (sustained attention). Overall reaction times were significantly faster after lumiVida™ vs. Control. (F(1, 52)=3.85, p<0.05 1-tail); difference denoted by different letters. Means are adjusted for baseline, age, NART errors, and test Day 1 reaction times at each trial block.

Figure 3:
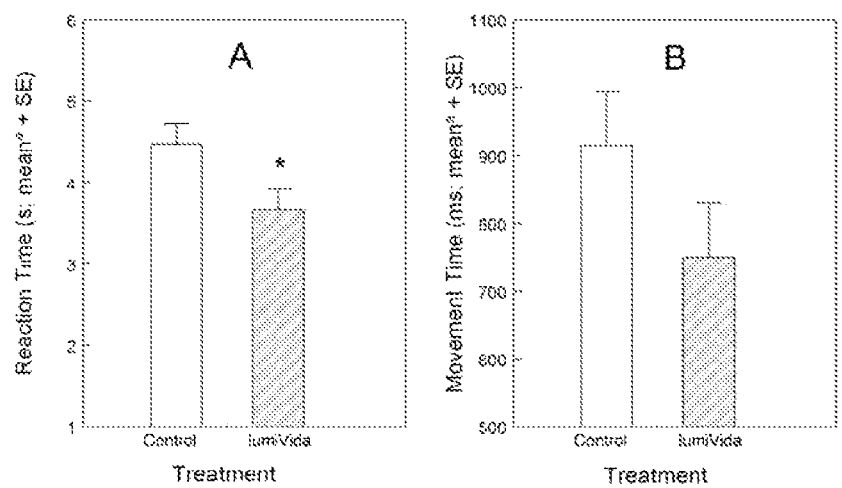

FIG. 3: Effect of lumiVida™ vs. Control treatment on reaction (A) and movement (B) times when given 8 choices. Reaction times were significantly faster after lumiVida™ on this complex choice task, *p<0.02. Raw movement time means are presented, although analysis was of Ln-transformed data. $^a$Means adjusted for baseline, age and NART errors.

Figure 4:
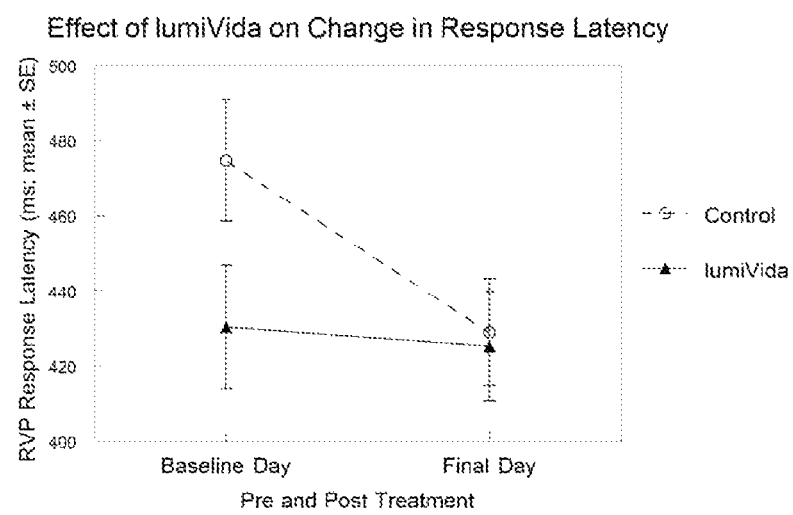

FIG. 4: Change in response latency for the RVP task before and after treatment, by treatment condition; see Example 3.

Figure 5:
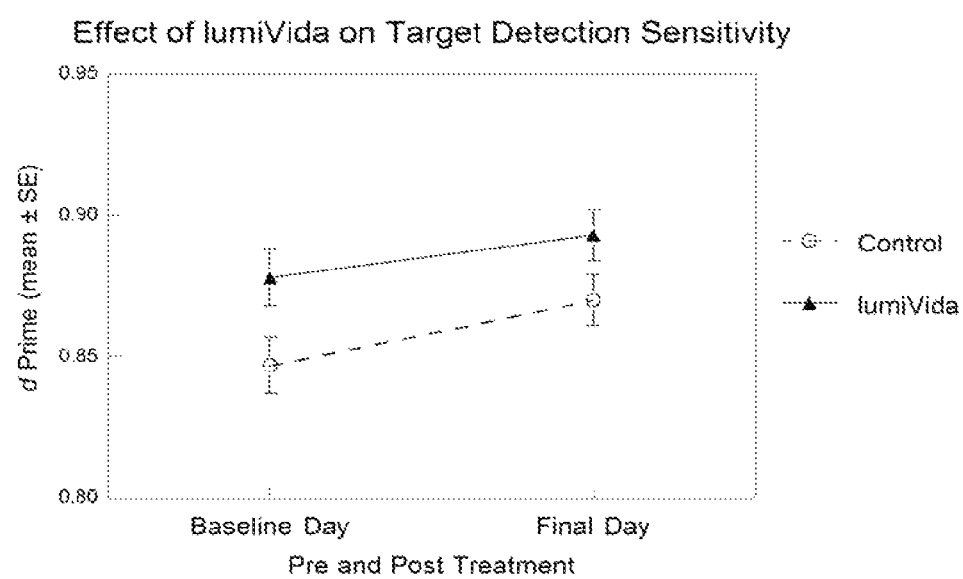

FIG. 5: Change in d Prime (signal detection theory measure of sensitivity to target detection) over test days by treatment condition.

Figure 6:
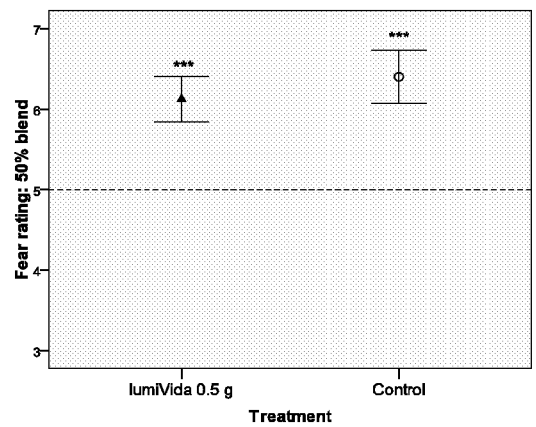
Figure 6:
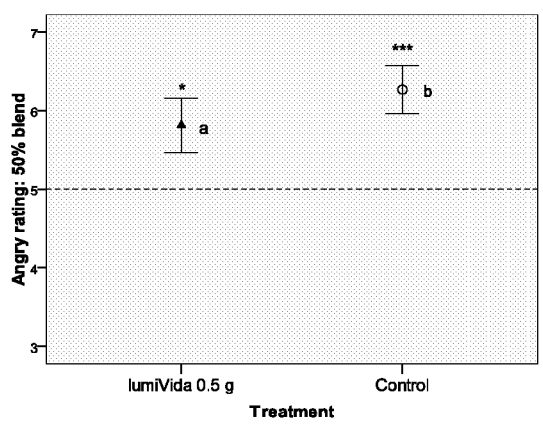
Figure 6:
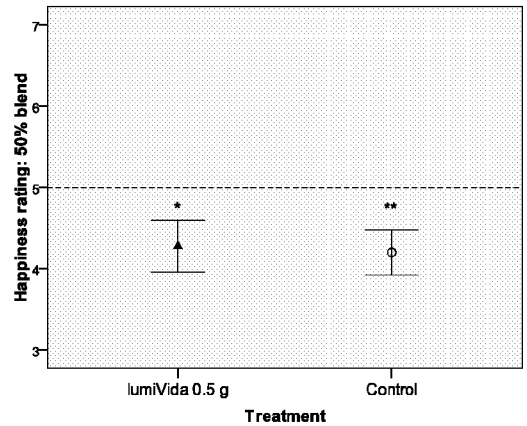
Figure 6:
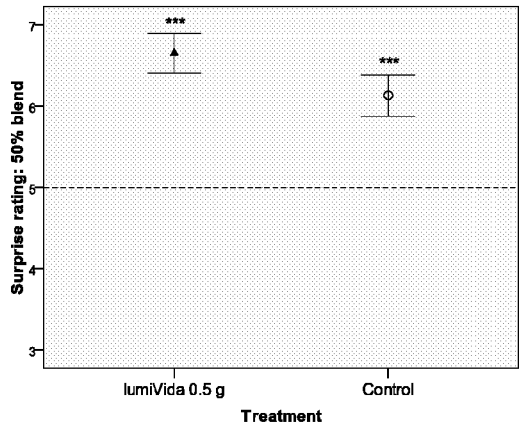

FIG. 6: Effect of lumiVida™ treatment on perception of particular emotions in faces with 50% blends of those emotions: A=Fear, B=Anger, C=Happiness, D=Surprise. The mid-point of 5 on the 1-9 scale represents accurate perception of 50% of the expression present (by comparison with the other % blends). Data are expressed as mean±SE for test Day 22 ratings, unadjusted for the first test day ratings. Significant differences from mid-point rating (broken line) are indicated (one-sample t tests), *p<0.05, p<0.01, *p<0.001; a, b—differing letters indicate significant differences between groups, adjusted for baseline data.

DEFINITIONS

"lumivida™" is a Trp-containing protein hydrolysate, specifically a hydrolyzed hens egg lysozyme composition which provides water soluble Trp containing peptides having a Trp/LNAA ratio of more than 0.15, and preferably between 0.18 and 0.23. It can be produced by hydrolyzing the lysozyme. Details are described WO 2008/052995, which is hereby incorporated by reference.

"Low dose" means that each dosage form of the lysozyme hydrolysate contains Trp containing di- or tri-peptides which provide 20-50 mg Trp per dose. It is recommended that 1-2 or more doses per day be consumed.

"Acute" means a single dosing.

"Chronic" means that the dosage forms are consumed over a period of time which is at least 19 days. Within the meaning of "chronic" are patterns of consumption which meet the definition of "substantially complied" (below).

"Substantially complied" means that, even if the person has missed a few dosages, the effects are still achieved. Specifically for a dosing regimen of 2 times per day for 19 days, a person who omits five or less non-consecutive dosings within this 19 day time period has substantially complied with the administration regime.

"Healthy" in context of this invention means that the person is in generally good health but wishes to boost their feeling of having high energy, increase in certain cognitive functions, especially sustained attention and faster reaction times, and information processing; quality of sleep; or feelings of well-being or happiness.

"Sorbet" means any frozen formulation which does not contain significant amounts proteins other than the Trp-containing protein hydrolysate, including ice, frozen lollies, frozen pops, popsicles, fruit ice lollies, slushies, snow cones and the like. While minor amounts may be present, a significant amount of protein will disturb the Trp/LNAA ratio unfavorably.

In previous reports of higher dosage administration of peptides/proteins which are a source of Trp, the feeling of having high energy was not reported by participants. Here, this was seen after a single dosing. This finding was especially unexpected as the low dose formulation was not seen to raise Trp/LNAA levels significantly, and in the past, high dosage Trp was seen to encourage/enhance sleep and sleep quality.

Thus, one aspect of this invention is a method of promoting a feeling of energy comprising consuming a low dose of a Trp-containing peptide at least twice per day for a chronic period of time. In preferred embodiments, the time period is at least 19 days, preferably at least 3 weeks, more preferably for at least one month.

The clinical trial reported in the Examples generated a number of significant results. Results from both the simple and complex (decision) reaction time tasks showed that lumiVida™ speeded up reactions and decision making, whilst accuracy was maintained. There was also some suggestion that this treatment may improve sustained attention. Interestingly, this would seem to be compatible with the stimulatory effect on mood ratings.

Serotonin is central to regulation of sleep, and TRP (at least at high doses) and alpha-lactalbumin have been shown to improve measures of quality and impact of sleep. In this chronic study with a low dose of lumiVida™, sleep quality is improved, and surprisingly, in the morning the Trp-containing peptide hydrolysate appears it to be somewhat stimulatory.

Furthermore, participants on 0.5 g lumiVida™ b.i.d. consistently reported feeling happier than those on the control treatment, prior to going to bed. This may be associated with the positive effects on emotional processing.

There were again some significant effects observed on emotional processing in the group receiving Trp-containing protein hydrolysate, suggest a shift in bias away from negative stimuli. Thus, the affective go/no go task found a reliable slowing of responses to negative words, including when the distractor words were only neutral, suggesting a disengagement with (less attention to) such negative emotional stimuli. The facial expression task results also support a shift away from attention to negative emotions (in particular anger) and a bias towards happiness.

Thus, one aspect of this invention is a method of promoting a feeling of well-being or happiness comprising consuming a low dose of a Trp-containing peptide at least once or twice per day for a chronic period of time. In preferred embodiments, the time period is at least 19 days, preferably at least 3 weeks, more preferably for at least one month.

The low dose food supplement, or nutraceutical can be consumed by healthy individuals who wish to experience an increase in a feeling of happiness or well-being, improved sleep quality and/or increase cognitive functions such as sustained attention and faster reaction times, and information processing. This chronic low dose ingestion would also be seen to benefit people who engage in activities which require an increase in concentration, creative thinking, quick, accurate decision making.

Suggested populations of people who would benefit from low doses of Trp-containing protein hydrolysates include: students, people involved in the creative arts, people whose professions require creative thinking or problem solving capabilities, people who feel under pressure to produce and those where thought processes are important. Non-limiting examples would include: engineers, writers, those in the advertising/sales/marketing industries, those in the entertainment industry, musicians, investigators, health care professionals such as nurses, emergency workers and physicians, researchers, salespersons, military and police personnel, and others.

Alternatively, the low dose Trp-peptides are suitable for people who would prefer to have a Trp-supplement as part of a food or drink which has a pleasant flavor and which consumed more than once per day.

Dosage Forms

The lysozyme hydrolysate may be in any form suitable for oral administration such as an additive to or supplement for feed or food, food or feed premix, tablets, pills granules, dragées, capsules, or effervescent formulations such as powders or tablets. It may also be in a liquid form such as a solution, gel, emulsion or suspensions as in beverages, sorbets, pastes or oily suspensions. Furthermore a multi-vitamin/mineral supplement may be added to the nutraceutical composition. Dietary supplements can also be extracts or concentrates, and may be found in many forms such as tablets, capsules, softgels, gelcaps, liquids, or powders. The lysozyme hydrolysate can also be added to other foodstuffs, including chocolate, ice cream, sorbets, soups and others. Dosage forms can be combined during the day in order to achieve the dosage; for example one may drink a beverage in the morning and have a sorbet in the evening; or a gel in the early afternoon and a beverage later in the day.

Preferred dosage forms include sachets containing instant drink beverage powders of the formulation which can be added to water, carbonated water, or other liquids, such has juices. Other preferred forms include nutritional gels and sorbets.

Another aspect of this invention is a method of promoting a feeling of energy increasing attention, promoting faster reaction times, promoting information processing, increasing quality of sleep and increased feelings or well-being or happiness comprising consuming a low dose of a Trp-containing peptide at least twice per day for a chronic period of time. In preferred embodiments, the time period is at least 19 days, preferably at least 3 weeks, more preferably for at least one month. Alternately, the low dose can be consumed in a variety of forms:

as part of a chronic consumption regime, i.e. one can consume a first form selected from the group consisting of a low dose lysozyme hydrolysate beverage and a second form which is other than a beverage. The doses may be consumed at different times during a 24 hour period.

in addition to a chronic low-dose consumption regime; i.e. a form can augment the dosage consumed.

Additionally, a higher dosage may be consumed as part of a chronic low dose regime or in addition to a chronic low dose regime, or in the absence of a chronic regime.

The low dose lysozyme hydrolysate of this invention can be consumed by healthy individuals who wish to experience an increase in a feeling of mental energy without interfering with normal sleep. People who wish to experience a sensation of "high energy" and are healthy may describe this feeling using terms such as 'buzzing/feel stimulated/hyper'; 'mind is racing'; and/or 'impulsive/spontaneous'. This chronic low dose ingestion would also be seen to benefit people who engage in activities which require an increase in concentration, creative thinking and high mental energy.

Beverage Forms

The beverages of this invention may be in the form of an instant beverage, wherein a powder mix, which is combined with a liquid to form the instant beverage. The liquid may be water, carbonated water, fruit juice, or other drink which will be acceptable to a consumer.

The powdered mix formulation of this invention comprises
  a) Trp-containing protein hydrolysate
  b) sweetening agent(s)
  c) flavoring agent(s); and
  d) optional extra nutritional ingredients In preferred drinks, the beverage may also contains citric acid in an amount required to impart a pleasant balance between the sweetener and acid taste. Exact amounts will vary depending on the taste properties of other mix ingredients, but it is well known how to determine optimal amounts. Other acids may be used in combination with or as a replacement or addition for citric acid include one or more of: malic acid, tartaric acid, fumaric acid, phosphoric acid, acetic acid (although this tends to impart a less pleasant flavor profile) and succinic and adipic acid (albeit to a lesser extent).

It may be desirable to produce a bulk powder which may be divided into individual servings or be sold in larger units. In addition to the hydrolysate, the powder formulation should contain a sweetener. This may be any conventionally used sweetener, such as sugar, sucralose, stevia-based sweeteners, and other available sweeteners, and mixes thereof. Typical amounts for 100 grams of formulated powder range from 50-85 grams sucrose plus sucralose, but this can vary.

In addition, the bulk powder may contain various flavors, either singly or in mixtures. For example, flavors may be fruit flavors, such as raspberry flavor, lemon flavor, blood orange, or strawberry flavor or other flavorings such as vanilla, coffee or chocolate. Fruit juice concentrates may also be used, such as apple concentrate, white grape concentrate, red grape concentrate, cranberry concentrate, blackcurrant concentrate, and mixtures thereof. Fruits, fruit blends, and fruit-vanilla blends are often preferred.

Other nutritional enhancers may be added if desired. For example, vitamins may be added, for example Vitamin B3, B5, B6, and/or B12 may be used. Vitamins C and E are recommended as good antioxidants.

Another liquid drink of this invention is as ready-to-drink beverage. This may be in the form of a shot, carbonated or non-carbonated drink, or any other form which is sold in a liquid form to the consumer. The dosings are the same as those above described for the powdered form.

Sorbet Forms

In addition to the Trp-containing hydrolysate, the sorbets of this invention will typically contain:
a) a sweetener or mixture of sweeteners-any available sweetener and/or sugar replacer can be used, (including maltitol, mannit, Isomalt, Lactit, Xylit) and combination of artificial sweeteners (aspartame, sucralose, cyclamate, saccharin and the like) with a filler such as glucose syrup can be considered, with the proviso that with sugar-alcohols the laxative properties have to be taken into account (20-30 g maximum per day). The optimal sweetner(s) will depend on the dosage of Trp-containing hydrolysate and the flavorings chosen. In one preferred embodiment a mixture of sorbitol, and fructose is used.

b) Citric acid—range will depend on flavor and regional preferences of the consumer. This can be readily determined. Other acids may be used in combination with or as a replacement or addition for citric acid include one or more of: malic acid, tartaric acid, fumaric acid, phosphoric acid, acetic acid (although this tends to impart a less pleasant flavor profile) and succinic and adipic acid (albeit to a lesser extent).

c) flavorings—any flavor may be used, fruit flavors are generally preferred and will depend largely on consumer acceptability. Coffee, chocolate, and tea are also preferred flavors.

The sorbets of this invention may be packaged in single dosage forms or may be packed in a bulk form where the consumer takes a desired amount from the bulk form. If packaged in a single dosage form, a scoop or similar utensil may be included in the packaging. For the bulk packaging, a doseage scoop is optionally included.

Nutritional Gels

Another aspect of this invention is a method of promoting
  a) an increased feeling of energy;
  b) increased certain cognitive functions, especially sustained attention and faster reaction times, and information processing;
  c) increased quality of sleep; or
  d) increased feelings of well-being or happiness
comprising consuming a low dose of a Trp-containing peptide in a nutritional gel at least ONCE? twice per day for a chronic period of time. In preferred embodiments, the time period is at least 19 days, preferably at least 3 weeks, more preferably for at least one month. Alternately, the low dose nutritional gel can be consumed:

As part of a chronic consumption regime, along with dosing forms which are other than nutritional gel (such as beverages, or sorbets, or included in other foodstuffs);

In addition to a chronic low-dose consumption regime.

Alternatively, a higher dosage may be consumed as part of a chronic low dose regime or in addition to a chronic low dose regime, or in the absence of a chronic regime.

As a gel form, it can be consumed during activities, in the same way as "sports gels", and the consumer need not worry about spillage. In another aspect of this invention, the nutritional gel can be added to water or other liquid to make a beverage. Further, elderly persons who cannot eat as much as would be required to maintain their health can also benefit from these gels (i.e. as medical nutrition foods). The nutritional gels of this invention may be packaged in single dosage forms or may be packed in a bulk form where the consumer takes a desired amount from the bulk form to re-package in single dosage forms. Preferably the package is an easy-to-open pouch or can be in a "squeeze" bottle.

In addition to the Trp-containing hydrolysate, the nutritional gels of this invention will typically contain:
  a) a sweetener or mixture of sweeteners—any available sweetener can be used, and the optimal one will depend on the dosage of Trp-containing hydrolysate and the flavorings chosen. In one preferred embodiment a mixture of maltrodextrin and sucralose is used. Normally the nutritional gels or energy gels have fast, medium and sometimes slow digestible carbohydrates to nourish the body during an exercise, so generally, monosaccharides, disaccharides and polysaccharides are combined in order to give energy to the body over a certain time. If sugar-alcohols are used, they should be used sparingly as they can have a laxative effect.

b) Citric acid or lactic acid may be used to impart a rounded flavor. Other acids may be used in combination with or as a replacement or addition for citric acid include one or more of: malic acid, tartaric acid, fumaric acid, phosphoric acid, acetic acid (although this tends to impart a less pleasant flavor profile) and succinic and adipic acid (albeit to a lesser extent).

c) flavorings—any flavor may be used, fruit flavors are generally preferred but any other popular flavor can be used such as coffee, tea, caramel, honey; choice will depend largely on consumer acceptability.

The following, non-limiting example better illustrates the invention.

EXAMPLES

Example 1

Clinical Trial

Design and Treatment

The design was a randomized, double-blind, placebo-controlled, between-subjects. Each group had 30 participants. The treatment conditions were either:

Placebo: Casein hydrolysate (primary milk protein hydrolysate; DSM Nutritional Products, Kaiseraugst, Switzerland) 0.52 g b.i.d was used to provide an intermediate amount of energy and total protein, in the placebo beverage, relative to the active treatments. It is appreciated from previous studies that casein hydrolysate is low in Trp and so will not raise serotonin synthesis.

lumiVida™ (DSM Nutritional Products, Kaiseraugst, Switzerland) is a hydrolyzed, enzymatic digest of a dietary protein (hen egg lysozyme) manufactured by using a proprietary mix of enzymes to provide a high quality source of peptides. The resulting protein hydrolysate (lumiVida™) contains a guaranteed minimum quantity of bioactive Trp-containing peptides. The ratio of these TRP peptides to peptides containing the Large Neutral Amino Acids (LNAA: Valine, Isoleucine, Leucine, Tyrosine, Phenylalanine) is approx. 0.2. LumiVida™ was taken as a citrus-flavored non-nutritively (Acesulfame) sweetened beverage given as 0.5 g lumiVida™ twice per day (b.i.d., i.e. 1 g lumiVida™ per day, which contains in total approx. 70 mg Trp per day).

Participants were randomly allocated, stratified by age, to either the placebo supplement group (N=30) or the lumiVida™ (0.5 g b.i.d.) supplement group (N=30). Both treatments were supplied in sachets of powder; each of these was stirred into approx. 150 ml tap water, forming a suspension. Double-blind randomization was carried out by means of a label code associated with a specific participant ID number, whose meaning is known only to the supplier. Participants were allocated randomly to these numbers.

The first testing took place on the screening day (baseline, Day 0) Subsequently, participants were supplied with 38 supplements (2 per day for 19 days) in the form of sachets of powder to be dissolved in 150 ml cold water. Participants were instructed to start taking the supplement on Day 3, so that Days 1 and 2 could be used to provide a pair of baseline sleep diary days prior to treatment. After 19 days of treatment, participants came back on Day 22 (test Day 2 (same test battery)), following one morning supplement dose on the final test day (timing as for first test day A single blood sample was taken on the baseline day, to establish pre-treatment levels of Trp and LNAA, for comparison with results at the end of treatment. On test Day 22, two blood samples were taken, i.e. before and after treatment, to determine whether fasting plasma Trp and Trp/LNAA levels were affected by the chronic treatment, and whether the single lumiVida™ (0.5 g) dose was effective in raising Trp/LNAA even after 19 days' treatment.

Results 59 female participants, aged 45-64 years (mean [SD] =53.9 [6.3]), completed pre- and post-treatment test sessions (Placebo N=30, lumiVida™ N=29). Although usually non-completers were replaced (treatment was stopped for 2 participants due to illness), one participant who failed to arrive for testing could not be replaced due to the end of feasible scheduling.

Main hypotheses: lumiVida™ would improve perceived energy levels.

Participants were asked to rate three times per assessment day various mental and physical sensations in a questionnaire (Mental and Physical Sensations (MAPS scale):

Three times at the baseline day (Day 0):
1. measurement at beginning of the day,
2. measurement 105 min later; and
3. measurement another 100 min later).

After 19 days lumiVida™ consumption (Day 22):
1. measurement at beginning of the day,
2. measurement 105 min later (90 min after the last placebo or treatment drink intake); and
3. measurement another 100 min later.

One factor of the MPAS scale was provisionally labeled "High Energy" after a Principal Component Analysis (PCA). Sensations of "high energy" were described using these terms: such as 'buzzing/feel stimulated/hyper'; 'mind is racing'; 'impulsive/spontaneous'.

Effects on High Energy

Ratings of High Energy were moderate. The baseline levels (first measurement on Day 1 and Day 22) did not differ between treatment groups, 1-way ANOVA group effect, $F(1, 57)<1$, variance explained $\eta_p^2=0.007$, NS; mean (SD): lumiVida™=3.03 (1.61), Control=3.29 (1.52).

Treatment condition had a small but significant effect on energy levels on the final test day, with higher overall energy ratings following chronic lumiVida™ treatment than after Control treatment, adjusting for baseline levels, ANCOVA treatment effect, $F(1, 54)=3.12$, $p<0.05$ 1-tail, $\eta_p^2=0.055$ (FIG. 1).

Combined ratings of 'high energy' (feeling stimulated, buzzing, impulsive, spontaneous) over all three test applications at the final test day were higher after chronic treatment with lumiVida™ than Control. These ratings did not change over the course of the final test day, i.e. were unaffected by the final drink.

Example 2

Clinical Trial

Design and Treatment

The design was a randomized, double-blind, placebo-controlled, between-subjects. Each group had 30 participants. The treatment conditions were either Placebo: Casein hydrolysate (primary milk protein hydrolysate; DSM Nutritional Products, Kaiseraugst, Switzerland) 0.52 g b.i.d was used to provide an intermediate amount of energy and total protein, in the placebo beverage, relative to the active treatments. It is appreciated from previous studies that casein hydrolysate is low in Trp and so will not raise serotonin synthesis.

lumiVida™ (DSM Nutritional Products, Kaiseraugst, Switzerland) is a hydrolyzed, enzymatic digest of a dietary protein (hen egg lysozyme) manufactured by using a mix of enzymes to provide a high quality source of peptides. The resulting protein hydrolysate (lumiVida™) contains a guaranteed minimum quantity of bioactive Trp-containing peptides. The ratio of these TRP peptides to peptides containing the Large Neutral Amino Acids (LNAA: Valine, Isoleucine, Leucine, Tyrosine, Phenylalanine) is approx. 0.2. LumiVida™ was taken as a citrus-flavored non-nutritively (Acesulfame) sweetened beverage given as 0.5 g lumiVida™ twice per day (b.i.d., i.e. 1 g lumiVida™ per day, which contains in total approx. 70 mg Trp per day).

Participants were randomly allocated, stratified by age, to either the placebo supplement group (N=30) or the lumiVida™ (0.5 g b.i.d.) supplement group (N=30). Both treatments were supplied in sachets of powder; each of these was stirred into approx. 150 ml tap water, forming a suspension. Double-blind randomization was carried out by means of a label code associated with a specific participant ID number, whose meaning is known only to the supplier. Participants were allocated randomly to these numbers.

The first testing took place on the screening day (baseline, Day 0) Subsequently, participants were supplied with 38 supplements (2 per day for 19 days) in the form of sachets of powder to be dissolved in 150 ml cold water. Participants were instructed to start taking the supplement on Day 3, so that Days 1 and 2 could be used to provide a pair of baseline sleep diary days prior to treatment. After 19 days of treatment, participants came back on Day 22 (test Day 2 (same test battery)), following one morning supplement dose on the final test day (timing as for first test day).

A single blood sample was taken on the baseline day, to establish pre-treatment levels of Trp and LNAA, for comparison with results at the end of treatment. On test Day 22, two blood samples were taken, i.e. before and after treatment, to determine whether fasting plasma Trp and Trp/LNAA levels were affected by the chronic treatment, and whether the single lumiVida™ (0.5 g) dose was effective in raising Trp/LNAA even after 19 days' treatment.

An additional facet was completion of a 'sleep diary', which asked questions about sleep quality and latency, and bed-time mood, as well as allowing recording of timing of supplement taking (see below).

59 female participants, aged 45-64 years (mean [SD]= 53.9 [6.3]), completed pre- and post-treatment test sessions (Placebo N=30, lumiVida™ N=29). Although usually non-completers were replaced (treatment was stopped for 2 participants due to illness), one participant who failed to arrive for testing could not be replaced due to the end of feasible scheduling.

Example 3

Effects of Chronic Intervention with lumiVida™ on Sleep and Evening Mood

Sleep was assessed using a self-completed printed 'diary'. The Sleep Diary contained 22 items, 16 of which were measured on a 100-mm visual analogue self-rating scale to assess various aspects of the previous night's sleep in comparison to usual sleep including sleep quality and latency (morning questions) and bed-time mood and alertness (evening questions).

These results concern the impact of chronic treatment on (a: post-treatment) any difference in sleep in the mean of the final 2 days of assessment during treatment (days 18 and 19) whilst controlling for baseline sleep using the mean of days 1 and 2 (prior to treatment) and (b: intervals during treatment) any change in sleep throughout treatment using the mean of days 4 and 5, 11 and 12, and 18 and 19.

Main hypotheses:
(a) Chronic lumiVida™ will improve sleep quality, reduce latency to fall asleep, and improve awakening from sleep.
(b) Chronic lumiVida™ would improve evening mood states.

Specific Approaches to Data Processing and Analysis

An average score was computed for each item from each pair of days (i.e. 1 & 2, 4 & 5, 11 & 12 and 18 & 19).

Several items, which compared responses to participants' "usual sleep", were based upon the Leeds Sleep Evaluation Questionnaire (SEQ) that provides a guide to item combinations as previously analysed using factor analysis, and were combined into composite measures as follows: the mean score of items relating to the question how would you compare getting to sleep last night compared to your usual sleep? (harder vs. easier; slower vs. quicker and less drowsy vs. more drowsy) were computed into 'getting to sleep'; items relating to the question 'how would you rate the quality of sleep last night compared with your usual sleep?' (more restless vs. more restful and awake more vs. awake less) were computed into 'Quality of sleep'; finally, items relating to the question 'how did your awakening compare with your usual pattern of awakening?' (more difficult vs. easier and took longer vs. shorter) were computed into 'Awakening from sleep'.

In addition, there were several items that were not referenced to "usual sleep", and these were analysed separately.

Evening questions relating to mood and alertness were analysed based upon Thayer's Energetic Arousal (computed as a mean score of items relating to the question 'how do you feel right now?'—tired/fatigued vs. energetic and drowsy/sleepy vs. alert), Tense Arousal (stressed/tense vs. relaxed/calm) and Hedonic Tone (down/dejected vs. happy).

The effect of treatment was analysed by comparing the dependent variable means for differences between treatment groups on the final pair of days after adjusting for baseline of pair of days (1 and 2). This is achieved by using analysis of covariance (ANCOVA) including baseline pair (days 1 and 2) variable as a covariate.

Change throughout duration of treatment was assessed using RMANCOVA, with each of the pair of days as the within-subjects factor, treatment group as the between-subjects factor and the baseline pair (days 1 and 2) as a covariate.

Quality of Sleep (e.g. How would You Rate the Quality of Sleep Last Night Compared with Your Usual Sleep?—Composite Measure)

Treatment condition altered the quality of sleep post-treatment, 1-way ANCOVA, Condition: $F(1, 56)=2.52$, $p<0.06$ 1-tail, $\eta_p^2=0.043$: there was a tendency for a better quality of sleep, compared to usual sleep experienced, at the end of chronic treatment with 0.5 g lumiVida™ vs. control (Table 1, below).

The quality of sleep at different intervals during treatment showed a weak interaction between time interval during treatment and condition ($F(1.78, 99.66)=2.40$, $p<0.05$ 1-tail, $\eta_p^2=0.041$; sphericity not assumed so adjusted using Greenhouse-Geisser). The quality of sleep tended to improve over treatment duration after 0.5 g lumiVida™ vs control (Table 1).

TABLE 1

Effect of lumiVida ™ on quality of sleep and difficulty
getting up throughout duration of treatment (100-mm scale)

| | | Quality of sleep | | | Difficulty getting up | | |
|---|---|---|---|---|---|---|---|
| Treatment | N | Days 4-5 Mean$^a$ (SE) | Days 11-12 Mean$^a$ (SE) | Days 18-19 Mean$^a$ (SE) | Days 4-5 Mean$^a$ (SE) | Days 11-12 Mean$^a$ (SE) | Days 18-19 Mean$^a$ (SE) |
| Control | 30 | 51.6 (0.23) | 55.5 (0.24) | 51.3 (0.23) | 60.1 (0.27) | 67.0 (0.33) | 59.0 (0.30) |
| lumiVida ™ | 29 | 46.6 (0.23) | 55.8 (0.24) | 56.5 (0.23) | 53.1 (0.28) | 61.5 (0.33) | 64.9 (0.30) |

$^a$adjusted for baseline.

Unreferenced Question: How would You Rate the Quality of Sleep Last Night? (Simple Measure)

Similarly to the composite measure, treatment condition marginally altered the quality of sleep post treatment, 1-way ANCOVA, Condition: $F(1, 56)=1.91$, $p<0.09$ 1-tail, $\eta_p^2=0.03$. There was a tendency for a better quality of sleep experienced after 0.5 g lumiVida™ vs control.

Unreferenced Question: Difficulty Getting Up (How Difficult was it to Get Up this Morning?—Not at all to Extremely)

Difficulty in getting up showed a weak interaction between time interval during treatment and condition, $F(2, 112)=2.96$, $p<0.03$ 1-tail, $\eta_p^2=0.05$. Self-rated 'difficulty in getting up' increased slightly over treatment duration after 0.5 g lumiVida™, whereas after control treatment a mid-treatment increase in difficulty then returned to baseline (Table 2, below). However, there was no difference by treatment condition for difficulty getting up on the last pair of days, $F(1, 56)<1$, ns, $\eta_p^2=0.004$.

Hedonic Tone (How do You Feel Right Now—Down/Dejected to Happy)

Treatment condition marginally altered hedonic tone post treatment, 1-way ANCOVA, Condition: $F(1, 56)=2.29$, $p<0.07$ 1-tail, $\eta_p^2=0.04$: A tendency for greater self-rated happiness was experienced after 0.5 g lumiVida™ vs. control. This was supported by a significant overall greater happiness (hedonic tone) for the lumiVida™ group during the chronic treatment, adjusted for baseline and unaffected by time (F<1), vs. control, $F(1, 56)=4.11$. $P<0.05$, $\eta_p^2=0.07$; Table 2, below).

TABLE 2

Effect of lumiVida ™ on overall hedonic tone
during treatment (100-mm scale)

| Treatment Group | N | Mean$^a$ (SE) |
|---|---|---|
| Control | 30 | 63.7 (0.23) |
| 0.5 g lumiVida ™ | 29 | 70.3* (0.23) |

$^a$adjusted for baseline.
*p < 0.05 for treatment group difference

Times Waking (How Many Times Did You Wake Restless During the Night)

The treatment condition marginally altered the number of times waking restless in the night post-treatment, 1-way ANCOVA, $F(1, 56)=2.21$, $p<0.07$ 1-tail, $\eta_p^2=0.04$: a tendency for fewer times waking was reported after 0.5-g lumiVida™ vs. control.

Performance (How Well do You Think You have Performed Today?)

Irrespective of treatment condition, self-reported performance during the day significantly increased over the duration of the study, particularly after the first week (Table 3, below: $F(2, 112)=4.25$, $p<0.02$, $\eta_p^2=0.07$).

TABLE 3

Increased self-reported performance over treatment duration
irrespective of treatment condition (100-mm scale)

| Days from start | Mean$^a$ (SE) |
|---|---|
| 4-5 | 62.1 (0.13) |
| 11-12 | 66.6 (0.20) |
| 18-19 | 66.8 (0.18) |

$^a$adjusted for baseline.

All Other Measures

There were no significant differences between conditions for whether participants were troubled by waking early and not getting back to sleep again at day 1 ($X^2=0.210$, ns.) or day 19 ($X^2=0.094$, ns.). Getting to sleep, awakening from sleep, how refreshed do you feel right now (morning), how refreshed compared to usual sleep, energetic arousal, tense arousal and latency to fall asleep did not vary significantly by treatment either post-treatment or during treatment (all F's(1,56)<1.40, ns, $\eta_p^2<0.035$).

Summary of Effects on Sleep and Daily Mood

LumiVida™ altered the quality of sleep, producing a tendency for a better quality of sleep throughout the duration of the treatment.

LumiVida™ also tended to increase self-rated difficulty in getting up over the duration of the treatment, but with no difference from control on the final diary days.

A tendency for greater self-reported happiness was experienced after lumiVida™, irrespective of treatment interval.

There was a tendency for fewer number of times waking restless during the night reported after lumiVida™

Perceived daily performance increased throughout the duration of the study regardless of treatment condition.

Example 4

Effects of Chronic Intervention with lumiVida™ on Cognitive Performance

Main hypotheses for the tests done—lumiVida™ would:
a) improve attention (e.g. improved accuracy without loss of speed)
b) improve sustained attention
c) improve memory General approach to data analysis The hypotheses are tested by comparing dependent variable means for significant differences between treatment groups on test Day 2 (Day 22), after adjusting for baseline performance (test Day 1). This is achieved using analysis of covariance (ANCOVA) including Day 1 performance as a covariate. In addition, age and NART errors are included as covariates. These latter variables did not differ by treatment group (Table 2.1), but could still contribute to variance in performance. For the Rotary Pursuit task, test Day 1 to test Day 2 change in performance is the key outcome, and so repeated-measures ANCOVA was used, with Day as the within-subject factor. In the SRT task, the two approaches were combined, in that RMANCOVA was used for the measure of sustained attention, i.e. change in reaction times over the last 3 quartiles of trials over the task period for test Day 2, but this was adjusted for test Day 1 (baseline) reaction times.

Data normality: where data were skewed >±1, each variable was transformed appropriately, e.g. positive skew reduced by natural log (Ln) or inverse transformation, before analysis.

Simple Reaction Time and Sustained Attention (SRT)

The Simple Reaction Time (SRT) test allows measurement of both overall simple reaction time and a measure of sustained attention. The test, running on E-Prime, lasts about 8 minutes, requiring participants simply to press the space bar as quickly as possible whenever they see an asterisk stimulus appear in the centre of the screen. The stimulus is presented in 64 trials, with a block of 16 trials presenting the stimulus at delays of 1, 2, 3, 4, 7, 9, 12 and 15 seconds, twice per delay, in random order. Preliminary analyses (on each day's data separately) confirmed that the first block (i.e. trials 1-16) may be regarded as a practice trial, while participants adjust to the task: thereafter, in the second block (trials 17-32), participants show the fastest reactions, and reaction time then increases over the remaining blocks, indicating fatigue and failure of sustained attention (Repeated Measures one-way ANOVA, effect of trial bins on unadjusted reaction times, day 1 $F(2, 114)=9.60$, $p<0.001$, day 2 $F(2, 114)=6.55$, $p<0.005$).

Therefore, the effect of lumiVida™ on sustained attention was examined by averaging reaction times within 4 bins over the 64 trials (1-16, 17-32, 33-48, 49-64), and analysing changes in reaction times over bins 2 to 4 (trials 17-64), when reactions tend to slow over time. It is also possible to group reaction times into those with 'short' (1-4 s) and 'long' (7-15 s) delays; however, preliminary analyses found no differences related to this grouping (Fs<1), so results are presented for overall averaged reaction times.

Effects on Simple Reaction Time

Chronic lumiVida™ treatment resulted in significantly faster simple reaction times compared to Control on test Day 2 (adjusted for baseline), $F(1, 51)=3.74$, $P<0.05$ 1-tail, $\eta_p^2=0.068$, (FIG. 2). Treatment did not significantly affect the change in reaction times over the trials, Condition×Bin interaction effect, $F(2, 102)=1.31$, NS, $\eta_p^2=0.025$. However, these results are adjusted for age, NART errors, and test Day 1 reaction times, and this adjustment removed the significant slowing of reaction times that would indicate a test of sustained attention, Trial bin effect, $F(2, 104)<1$, NS, $\eta_p^2=0.011$. The unadjusted effect of Bin was significant, $F(2, 112)=6.56$, $p<0.01$, $\eta_p^2=0.105$, with average reactions for Bins (blocks) 3 and 4 being slower than for Bin 2 (Bonferroni-adjusted comparisons, $p<0.05$, $0.001$, respectively).

Summary

This task assessed both simple reaction times, and a measure of sustained attention. lumiVida™ significantly increased the speed of simple reaction times. There was a tendency for lumiVida™ to improve sustained attention, given the significantly faster reactions on the final block of trials.

Match to Sample Visual Search (MTS)

Match to Sample Visual Search (MTS) is a visual pattern matching test, with a speed/accuracy trade-off. It is a visual search task with response latency dissociated from movement time. Efficient performance on this task requires the ability to search among the targets and ignore the distractor patterns which have elements in common with the target.

The participant is shown a complex visual pattern (the sample) in the middle of the screen, and then, after a brief delay, a varying number of similar patterns is shown in a circle of boxes around the edge of the screen. Only one of these boxes matches the pattern in the centre of the screen, and the participant must indicate which it is by touching it. There are a total of 18 test trials: 6 trials with 2 choices, 6 with 4 choices and 6 with 8 choices. Reaction time is measured as the time from the pattern choices being revealed to the release of the press-pad on which their finger rests between tests. By contrast, movement time is measured as the time between release of the press-pad and touching of the target pattern. The former is therefore primarily a measure of task processing and decision time; the latter reflects response movement control and speed.

Total correct matches, and movement time variables, were skewed, and so were transformed (see below). ANCOVAs were carried out on those transformed variables, but means are presented for untransformed variables, adjusted for covariates (baseline, age, NART errors).

Effects on Overall Total Correct Matches

At each test session, participants performed 18 trials: on average accuracy was very good, achieving at least 17 mean correct matches. Therefore, this outcome is unlikely to be sensitive to improved performance, and this was reflected in a lack of treatment effect (Table 2.15), ANCOVA group effect, $F(1, 54)<1$, NS, $\eta_p^2=0.007$.

Effects on Overall Reaction Times (Correct Targets)

Chronic treatment with lumiVida™ significantly increased the speed of reaction times for correct target choices (first attempt), compared to Control (Table 4, below), ANCOVA group effect, $F(1, 54)=3.97$, $p=0.025$ 1-tail, $\eta_p^2=0.068$.

Effects on Overall Movement Times (Correct Targets)

Treatment with lumiVida™ resulted in slightly faster overall movement times for correctly chosen targets, but the difference from Control was not significant (Table 4), ANCOVA group effect, $F(1, 54)<1$, NS, $\eta_p^2=0.006$.

TABLE 4

Effect of lumiVida ™ on Total Correct Pattern Matches, Reaction and Movement Times

| Treatment Group | N | Total Correct (N targets/18) Mean$^a$ (SE) | Reaction Time (Correct; s) Mean$^a$ (SE) | Movement Time (Correct; ms) Mean$^a$ (SE) |
|---|---|---|---|---|
| Control | 30 | 17.4 (0.15) | 2.936 (0.146) | 735.1 (33.5) |
| lumiVida ™ | 29 | 17.3 (0.15) | 2.519* (0.149) | 698.2 (34.1) |

$^a$adjusted for baseline, age and NART errors.
*p < 0.05, lumiVida ™ vs. Control.

Effects on Reaction and Movement Times—8 Choices

The most demanding trials were those with 8 possible target choices. These trials are more likely to be sensitive to improvement, so their outcomes are examined separately here.

Reaction times with 8 choices were significantly faster after lumiVida™, ANCOVA group effect, $F(1, 54)=4.88$, $p<0.02$ 1-tail, $\eta_p^2=0.083$. lumiVida™ treatment also reduced movement times with 8 choices, but not significantly (FIG. 3), ANCOVA group effect, F(1, 54)=2.20, p=0.07 1-tail, $\eta_p^2$=0.039. FIG. 3 shows the effect of lumiVida™ vs. Control treatment on reaction (A) and movement (B) times when given 8 choices. Reaction times were significantly faster after lumiVida™ on this complex choice task, *p<0.02. Raw movement time means are presented, although analysis was of Ln-transformed data. [a]Means adjusted for baseline, age and NART errors.

Effects on Reaction and Movement Times for Tasks with 8 vs. 2 Target Choices

These outcomes assess the impact of the complexity of additional target choices (8 vs 2) on response times.

Treatment significantly affected the increase in reaction times from 2 to 8 choices, with a smaller increase after lumiVida™, reflecting the faster reaction times in the 8-choice situation (Table 5), ANCOVA group effect, F(1, 54)=5.34, p<0.02 1-tail, $\eta_p^2$=0.090.

Similarly, lumiVida™ treatment resulted in a smaller increase in movement time from 2 to 8 choices, but this did not reach significance (Table 2.16), ANCOVA group effect, F(1, 54)=2.44, p=0.06 1-tail, $\eta_p^2$=0.043. These data were skewed and so were analysed as square-root-transformed data.

TABLE 5

Effect of lumiVida ™ on Increase in Reaction and Movement Times for 8 vs. 2 Target Choices

| Treatment Group | N | Reaction Time (change; s) Mean[a] (SE) | Movement Time[b] (change; ms) Mean[a] (SE) |
|---|---|---|---|
| Control | 30 | 2.823 (0.224) | 290.1 (75.7) |
| lumiVida ™ | 29 | 2.097* (0.220) | 130.4 (77.0) |

*p < 0.02, lumiVida ™ differs from Control.
[a]adjusted for baseline, age and NART errors.
[b]Movement data were transformed for analysis.

Summary

Reaction times were significantly faster after lumiVida™, both overall and for the most complex 8-choice task. A similar non-significant trend was seen for movement times. High overall accuracy in this task suggests it may not have been sensitive to any improvement in performance accuracy. lumiVida™ produces faster choice response times, especially for the time involved in deciding which stimulus is the correct target. Also, this faster response does not reduce accuracy.

Rapid Visual Information Processing Task (RVP)

Rapid Visual Information Processing (RVP) is a test of sustained attention and working memory. It is sensitive to dysfunction in the parietal and frontal lobe areas of the brain and is also a sensitive measure of general performance.

A white box appears in the centre of the computer screen, inside which digits, from 2 to 9, appear in a pseudo-random order, at the rate of 100 digits per minute (the task lasts about 6 minutes). Participants are requested to detect target sequences of digits (for example, 2-4-6, 3-5-7, 4-6-8) and to press a key pad only when they have detected the third digit from any one of these sequences. In a block of 100 digit presentations, there are 3 of each target sequence, i.e. 9 target sequences per block: total scores are derived from the final three blocks, i.e. 27 target sequences. As only the last digit in each target sequence should be responded to, there are 273 non-target stimuli in total.

There is a substantial practice period included in this task; nevertheless, participants often find the task demanding. In this study, 6 participants had to be excluded as they were unable to follow the instructions or refused to complete the task (TC14, TC18, TC20, TC29, TC38, TC48): there were 3 non-completers excluded from each treatment condition, and no evidence for any differences by age or NART score from the completing participants.

Assessment of performance is derived from the last three blocks (5, 6, 7)). The RVP outcome measures of interest cover latency to respond, total hits, total false alarms (responding to non-targets), and detection sensitivity based on the standardised difference in probabilities of hits and false alarms ('d prime', calculated by the software using Signal Detection Theory).

Baseline Measures

Despite random allocation to condition, several variables on this test differed between treatment groups at baseline, either significantly or close to significance: response latency (F(1, 51)=3.62, p=0.06); total hits (F(1, 49)=3.45, p=0.07, and detection sensitivity (d prime: F(1, 49)=4.70, p<0.05), though not total false alarms (F<1). This makes results from the usual ANCOVA on final test performance controlling for baseline open to misinterpretation. Thus these variables (except false alarms) were analysed using RMANOVA, with pre- and post-treatment as the within-subjects factor, and age and NART as covariates.

Effects on Response Latency

Response latencies (reaction time to respond correctly to targets) were slower at pre-treatment baseline for the Control group than for the lumiVida™ group, but on the final test day this difference had gone, largely due to a reduction in response time for the Control group, while response latencies for the lumiVida™ group only decreased slightly, Pre/Post×Treatment interaction, F(1, 49)=7.70, p<0.01 (FIG. 4). Neither Pre/Post nor treatment main effects were significant (F=2.23, F=1.37, respectively), with age and NART as covariates.

Effects on Total Hits

Out of a maximum of 27 target sequences, the overall average hits (correct responses) were: Test Day 1 mean (SE)=18.5 (0.65), Test Day 2 mean (SE)=20.8 (0.58). This suggests a reasonable level of accuracy on average, but with room for improvement. The overall increase in hits from test Day 1 to test Day 2 (Table 6, below) was significant for pairwise comparisons of the adjusted means (p<0.001), but the main Pre/Post effect was not significant with age and NART errors included as covariates (F(1, 49<1, NS, $\eta_p^2$=0.00). There was no effect of treatment on the change in hits from baseline to final test day, Pre/Post x treatment interaction, F(1, 49)=1.46, NS, $\eta_p^2$=0.029, nor any overall treatment group difference, F(1, 49)=2.57, NS, $\eta_p^2$=0.05.

Effects on Total False Alarms

Total false alarms were rare, averaging less than two false alarms (Table 6), implying accurate discrimination of targets by most participants. Not surprisingly, treatment did not significantly affect false alarm rate on the final test day, ANCOVA Condition effect, F(1, 48)=1.72, NS, $\eta_p^2$=0.035. These analyses were carried out on Ln-transformed variables, due to positive skews of the raw total false alarm variables; however, the raw means are presented for ease of interpretation.

TABLE 6

Effect of Chronic lumiVida™ on Total Hits and Total False Alarms on Day 2

| Treatment Group | N | Total Hits (Pre and Post-treatment) Mean$^a$ (SE) | | Total False Alarms$^c$ Mean$^b$ (SE) |
|---|---|---|---|---|
| | | Day 1 | Day 2 | Day 2 |
| Control | 27 | 17.2 (0.91) | 20.2 (0.81) | 1.66 (0.36) |
| lumiVida ™ | 26 | 19.7 (0.93) | 21.4 (0.83) | 1.39 (0.37) |

$^a$adjusted for age and NART errors;
$^b$Adjusted additionally for baseline.
$^c$Analysed as Ln-transformed, adjusted data.

Effects on Detection Sensitivity

The signal detection measure of sensitivity, d prime (RVP A), increased slightly overall from before to after treatment (significant pairwise pre/post comparison, p=0.012), though the Pre/Post main effect was not significant after adjusting for age and NART, F(1, 49)=1.34, NS, $\eta_p^2$=0.027

However, treatment condition did not affect this change, Pre/Post x treatment interaction, F(1, 49)<1, NS, $f_p^2$=0.006. Nevertheless, the main effect of treatment condition was significant, F(1,49)=5.32, p<0.05, $\eta_p^2$=0.098, indicating that the greater d prime mean for the lumiVida™ group at baseline was maintained to post-treatment. The lumiVida™ group was more sensitive at baseline and remained so on the final test day, with no evidence that chronic treatment had any specific impact other than a small overall improvement (see Example 3).

Summary of Rapid Visual Information Processing Task

For several variables, there were marginal differences at baseline between treatment groups, despite randomisation, that could affect interpretation of any change over chronic treatment. Therefore, those variables were analysed by repeated measures ANOVA, to determine whether any change from before to after chronic treatment was dependent on the treatment condition.

Slower response latencies seen in the Control group at baseline became faster on the final test day, so that they became similar to those seen for the lumiVida™ group. There was no evidence that lumiVida™ altered response times.

Performance accuracy measures (total hits and false alarms) were not significantly affected by lumiVida™ treatment.

The measure of detection sensitivity, d prime, was consistently higher for the lumiVida™ group at before and after treatment, but treatment itself did not appear to alter this, relative to Control.

Example 5

Emotional Processing

Effects of chronic intervention with lumiVida™ on Facial Emotional Expression Rating Task Main hypotheses on this test—lumiVida™ would:
(a) Reduce sensitivity to negative emotional expressions;
(b) Increase sensitivity to positive emotional expressions.

This task assesses subjective perception of positive and negative social stimuli, i.e. facial expressions of six basic emotions, fear, anger, sadness, happiness, surprise and disgust. The task is run on a PC using E-Prime, and presents participants with black and white images of a male face, front on, one face at a time. The expressions on the face are arrayed in blends of two emotions varying in ratios of 10%, 30%, 50%, 70%, and 90%. Participants are asked to rate each face for the intensity of one of the emotions, on a 9-point scale from 1='not at all [emotion]' to 9='very [emotion]'. Each emotion is blended separately with two others in this way, thus providing an average rating of perceived emotional intensity over 10 faces of varying blends. However, the rated response to the two 50% blends for each emotion (e.g. fear with sadness and surprise) should provide the most reliable measure of perceptual bias, so these are analysed separately.

General Approach to Data Analysis

The hypotheses are tested by comparing dependent variable means for significant differences between treatment groups on test Day 2 (day 22), after adjusting for baseline performance (Day 1) (ANCOVA). In addition, for the 50% blend data, one-sample t tests were used to test for mean differences from the scale mid-point of 5, as a measure of accuracy of emotional perception.

For this test, subjective ratings of emotional intensities are the dependent variables, so age and NART errors are not included as covariates; these latter variables did not differ by treatment. Including trait neuroticism as a covariate did not alter the findings, so the unadjusted results are presented here. The dependent variables and covariates reported here were not skewed, so raw scores were analysed.

Effects on Anger

Treatment condition significantly altered rated intensity of expression of anger in 50% blended faces, 1-way ANCOVA, F(1, 56)=6.13, p=0.016, $\eta_p^2$=0.099 (Table 7, below): rated anger was less after lumiVida™ vs. Control, and the mean rating was more accurate, being closer to 50% (FIG. 5). For the overall average anger rating, there was no effect of treatment condition, F<1, ns, $\eta_p^2$=0.012.

Effects on Happiness

Although there was no significant effect of treatment on happiness ratings for 50% blended faces (FIG. 6): F<1, ns, $\eta_p^2$=0.007), there was a significant effect of treatment condition on ratings of overall happiness F(1, 56)=4.24, p=0.044, $\eta_p^2$=0.07: rated happiness perception was greater after 0.5 g lumiVida™ vs. Control (Table 2.11).

Effects on Surprise

There was a weak effect of treatment condition on ratings of surprise for 50% blends, F(1, 56)=3.46, p<0.07 2-tail, $\eta_p^2$=0.06; rated surprise tended to be greater after lumiVida™ vs. Control (FIG. 6). For the overall surprise rating, there was no effect of treatment condition, F<1, ns, $\eta_p^2$=0.01.

Effects on Sadness

There was no effect of treatment on sadness ratings for 50% blended faces (Table 7: F<1, ns, $\eta_p^2$=0.00), nor on overall sadness ratings (Table 8: F<1, ns, $\eta_p^2$=0.011).

1.1.1.1 Effects on Fear

There was no effect of treatment on fear ratings for 50% blended faces (FIG. 6: F<1, ns, $\eta_p^2$=0.000), nor on overall fear ratings (Table 8: F<1, ns, $\eta_p^2$=0.018).

1.1.1.2 Effects on Disgust

There was no effect of treatment on disgust ratings for 50% blended faces (Table 7: F(1, 56)=2, ns, $\eta_p^2$=0.004), nor on overall disgust ratings F<1, ns, $\eta_p^2$=0.013).

TABLE 7

Effect of lumiVida ™ on Ratings of Emotional Expressions
with 50% blends: Data are Means[a] (SE) over 10 blends

| Treatment Group | N | Anger | Happy | Surprise | Sadness | Fear | Disgust |
|---|---|---|---|---|---|---|---|
| Control | 30 | 6.49 (0.26) | 4.13 (0.26) | 6.10 (0.2) | 5.56 (0.32) | 6.29 (0.26) | 6.17 (0.31) |
| lumiVida ™ | 29 | 5.58 (0.26) | 4.35 (0.26) | 6.69 (0.23) | 5.53 (0.33) | 6.23 (0.27) | 5.98 (0.31) |

[a] adjusted for baseline.

TABLE 8

Effect of lumiVida ™ on Total Ratings of Emotional
Expressions: Data are Means[a] (SE) over 10 blends

| Treatment Group | N | Anger | Happy | Surprise | Sadness | Fear | Disgust |
|---|---|---|---|---|---|---|---|
| Control | 30 | 5.71 (0.14) | 4.71 (0.22) | 6.02 (0.15) | 5.07 (0.18) | 5.89 (0.18) | 5.68 (0.18) |
| lumiVida ™ | 29 | 5.54 (0.14) | 5.11* (0.14) | 6.18 (0.15) | 5.28 (0.19) | 6.14 (0.18) | 5.91 (0.19) |

[a] adjusted for baseline.
*$p < 0.05$ for greater rated happiness overall after lumiVida ™.

Example 6

Raspberry Lemonade Lumivida Instant Beverage

A typical instant beverage will contain:

| Ingredient | Grams |
|---|---|
| Per 480 ml water | |
| Sucrose | 14.4 |
| Citric Acid | 1 |
| Raspberry Flavor | 0.05 |
| Lemon Flavor | 0.05 |
| LUMIVIDA | 2 |
| Sucralose | 0.05 |
| TOTAL | 17.55 |

| INGREDIENT For 100 g powder | |
|---|---|
| Sucrose | 82.5 |
| Citric acid | 5.7 |
| Raspberry Flavor | 0.285 |
| Lemon Flavor | 0.285 |
| LUMIVIDA | 11.4 |
| Sucralose | 0.285 |
| TOTAL | 100 |

Example 7

Blood Orange Flavored Ready-to-Consume Carbonated Drink

A typical ready-to-consume carbonated drink will contain:

| Ingredient | Amount g/kg |
|---|---|
| Sucrose Granulated | 100.00 |
| Sodium Benzoate | 0.18 |
| Citric Acid | 2.50 |
| Ascorbic Acid | 0.20 |
| Blood Orange Flavor | 2.00 |
| Beta Carotene 10% CWS/S(stock solution 1 mg/ml) | 2.00 |
| Lumivida | 1.93 |
| Calcium D Pantothenate (B5) | 0.01004 |
| Pyridoxine Hydrochloride (B6) | 0.00200 |
| B12 0.1% WS | 0.00602 |
| Niacinamide (B3) | 0.02004 |
| Water De-ionized and carbonated | 891.15 |
| Total | 1000.00 |

Serving size: 200-300 ml

Example 8

Berry Blend Shot

A typical shot will contain:

| Ingredient | Grams | % Juice |
|---|---|---|
| Apple concentrate | 30 | 18.5 |
| White grape concentrate | 20 | 8.3 |
| Red grape concentrate | 20 | 8.3 |
| LUMIVIDA | 8.33 | |
| Cranberry Concentrate | 7.5 | 5.1 |
| Blackcurrant Concentrate | 7.5 | 9.8 |
| Citric Acid | 3 | |
| Strawberry Flavor | 1 | |
| Stevia sweetener | 0.5 | |
| Water | 902.2 | |
| TOTAL | 1000 | 0.5 |

SERVING SIZE: 60 ml

Example 9

Fruit Shot

A typical fruit flavored shot may contain:

| Material in g | 0.5 g/serving LumiVida | 1 g/serving LumiVida |
|---|---|---|
| Water | 985.680 | 973.380 |
| Sucralose | 0.400 | 0.400 |
| Lemon flavor | 0.800 | 0.800 |
| Raspberry flavor | 0.020 | 0.020 |
| Potassium sorbate | 0.000 | 0.000 |
| Lactic acid (45% w/w) to pH = 3.6 | 4.800 | 8.700 |
| LumiVida | 8.300 | 16.700 |
| Total | 1000.000 | 1000.000 |

Preparation:

Mix the dry ingredients

Mix the water with the Potassium Sorbate and add the dry ingredients

Add the Lactic Acid solution and set on pH 3.6

Add the flavours

Fill into PET bottles

Pasteurisation 72° C. for 2 minutes

Example 10

Grapefruit Flavored Sorbet

A typical sorbet will contain:

| Material in g | 0.5 g/serving LumiVida | 1 g/serving LumiVida |
|---|---|---|
| Sorbitol | 128.000 | 124.000 |
| Fructose | 76.120 | 74.240 |
| Citric acid solution 50% w/w | 5.000 | 5.000 |
| Stabilizer Meyprogen IC Universal-a hydrocolloid/emulsifer containing stabilizer | 5.000 | 5.000 |
| Grapefruit juice concentrate | 23.000 | 23.000 |
| Grapefruit Flavor | 0.500 | 0.500 |
| b-Carotene 10% EM R as 1% Solution | 11.250 | 11.250 |
| Water | 745.250 | 745.250 |
| LumiVida trp-containing hydroysate | 5.880 | 11.760 |
| Total | 1000.000 | 1000.000 |
| Total content PF in g/85 g (serving) | 0.50 | 1.00 |

Preparation:

Dissolve sorbitol, fructose and stabilizer at 40° C. in water. Add color solution and juice concentrate Heat to 75° C., leave for 15 min at this temperature. Homogenize hot in a high pressure homogenizer at 30 bar. After homogenizing cool down the mixture immediately to 5° C. Add citric acid and flavor. Pass through ice cream machine with 50% overrun; Fill into containers; freeze.

Example 11

Ice Lollies/Popsicles

A typical ice lolly or popsicle will contain

| Ingredients | [g] |
|---|---|
| Sugar | 150.0 |
| Glucose syrup ~DE 38 | 60.0 |
| Citric acid as a 50%(w/w) solution | 18.0 |
| Stabilizer (plant hydrocolloids) | 5.0 |
| Lemon/Orange flavour | q.s. |
| lumiVida | 5.880 |
| Water to | 1000.0 |

Preparation

Preblend all dry ingredients in an appropriate mixer. Dissolve the premix in the water under stirring. Heat the liquid mix to 50° C. before adding the glucose syrup. Homogenize the mix in a high pressure homogenizer (p1 150 bar/p2 50 bar) and pasteurize in a plate heat exchanger at 80° C. for 15 sec. Cool the mix to 5° C., then add flavour and citric acid. Fill the mix into forms and freeze at −25° C.
Serving size 85 g→0.5 g lumivida/85 g

Example 12

Lemon Raspberry Nutritional Gel

A typical nutritional gel will contain

| Material in g | 0.5 g/serving LumiVida | 1 g/serving LumiVida |
|---|---|---|
| Water | 360.0 | 350.0 |
| Maltodextrin DE 20 | 601.9 | 599.4 |
| Sucralose | 0.3 | 0.3 |
| Lemon flavour | 1.0 | 1.0 |
| Raspberry flavour | 0.04 | 0.04 |
| Potassium sorbate | 0.25 | 0.25 |
| Lactic acid (45% w/w) to pH = 3.6 | 24.0 | 24.0 |
| LumiVida Trp-rich hydrolysate | 12.5 | 25.0 |
| Total | 1000 | 1000 |
| Total content hydrolysate per 40 g (serving) | 0.50 | 1.00 |

Preparation:

Mix the sucralose and the sorbate. Mix a part of the water (app. 300 g) with the Potassium Sorbate/sucralose. Add a part Lactic Acid solution and set on pH 3.6. Add the maltodextrin mix all in a Stephan Mixer with 1000 ppm for 2 minutes and 3000 ppm for 7 minutes. Mix the LumiVida and the flavours with the remaining water (app. 70 g). Add the flavours/water solution. Set on pH 3.6 with the remaining part of Lactic Acid solution. Mix with the 1st part of the water/Potassium Sorbate/sucralose mixture. Check pH. Fill into desired packages. Pasteurization is for 5 minutes 80° C.

The invention claimed is:
1. An edible composition which imparts a feeling in a healthy adult consumer which is selected from the group consisting of:
 a) increased energy;
 b) an increase in certain cognitive functions including, sustained attention, faster reaction times, and information processing;

c) increased quality of sleep; or
d) increased feelings of well-being or happiness, wherein the composition is a pharmaceutical, food or food supplement comprising a hen egg lysozyme tryptophan-containing hydrolysate (Trp-containing protein hydrolysate) having a ratio (Trp/LNAA) of tryptophan (Trp) to large neutral amino acid (LNAA) of greater than 0.15, and wherein the dosage of the Trp-containing protein hydrolysate provides 10-100 mg of Trp per day.

2. The edible composition according to claim 1, wherein the composition is a beverage, a sorbet or a nutritional gel.

3. The edible composition according to claim 1, wherein the composition is an instant beverage powder which further comprises:
   a) a sweetening agent;
   a) a flavoring agent; and
   a) optional extra nutritional ingredients.

4. The edible composition according to claim 1, wherein the composition is a beverage which further comprises at least one acid selected from the group consisting of citric acid, malic acid, tartaric acid, fumaric acid, phosphoric acid, acetic acid, succinic acid and adipic acid.

5. The edible composition according to claim 1, wherein the composition is a sorbet which further comprises:
   a) a sweetener or mixture of sweeteners;
   b) citric acid and optionally least one additional acid selected from the group consisting of malic acid, tartaric acid, fumaric acid, phosphoric acid, acetic acid, succinic acid and adipic acid; and
   c) flavorings.

6. The edible composition according to claim 1, wherein the composition is a nutritional gel which further comprises:
   a) a sweetener or mixture of sweeteners;
   b) citric acid or lactic acid, or optionally at least one acid selected from the group consisting of malic acid, tartaric acid, fumaric acid, phosphoric acid, acetic acid; succinic acid, and adipic acid; and
   c) flavoring.

7. A method to impart in a healthy adult consumer a feeling selected from the group consisting of:
   a) increased energy
   b) an increase in certain cognitive functions, especially sustained attention and faster reaction times, and information processing; or
   c) increased quality of sleep; and
   d) increased feelings of well-being or happiness, wherein the method comprises administering to a healthy adult consumer an effective amount of the edible food composition according to claim 1.

8. A method of increasing:
   a) a feeling of energy;
   b) cognitive functions selected from the group consisting of sustained attention, faster reaction times, and information processing;
   c) quality of sleep; or
   d) feelings of well-being and happiness in a healthy adult, wherein the method comprises administering to the healthy adult a pharmaceutical, food or food supplement comprising a hen egg lysozyme tryptophan-containing hydrolysate (Trp-containing protein hydrolysate) having a ratio (Trp/LNAA) of tryptophan (Trp) to large neutral amino acid (LNAA) of greater than 0.15, and wherein the dosage of the Trp-containing protein hydrolysate provides 10-100 mg of Trp per day.

9. The method according to claim 8, wherein the pharmaceutical, food, or food supplement is a beverage, a sorbet, or a nutritional gel.

10. A single dose composition which is a beverage, a beverage powder, a gel, or a sorbet comprising:
    a) less than 4000 mg per dosage of a hen egg lysozyme tryptophan-containing hydrolysate (Trp-containing protein hydrolysate) having a ratio (Trp/LNAA) of tryptophan (Trp) to large neutral amino acid (LNAA) of greater than 0.15;
    b) a sweetening agent;
    c) a flavoring agent; and
    d) optional extra nutritional ingredients.

11. The composition according to claim 10, wherein the amount of the Trp-containing protein hydrolysate per dosage is 2000 mg to 4000 mg.

12. The composition according to claim 10, wherein the amount of the Trp-containing protein hydrolysate is 1000 mg.

13. The composition according to claim 10, wherein the amount of the Trp-containing protein hydrolysate is 400-600mg.

14. The composition according to claim 10, wherein the amount of Trp-containing protein hydrolysate is sufficient to provide at least 10 mg Trp per day but less than 400 mg Trp per day.

15. The composition according to claim 10, wherein the amount of the Trp-containing hydrolysate is sufficient to provide at least 25 mg Trp per day but less than 350 mg Trp per day.

16. The composition according to claim 10, wherein the composition is a beverage or beverage powder.

17. The composition according to claim 10, wherein the composition is a beverage selected from the group consisting of instant beverages, beverage shots, still drinks and carbonated drinks.

18. The composition according to claim 10, wherein the composition is a beverage powder which further comprises an acid selected from the group consisting of citric acid ,malic acid, tartaric acid, fumaric acid, phosphoric acid, acetic acid, succinic acid, adipic acid and mixtures thereof.

19. An instant beverage which comprises an admixture of the beverage powder of claim 18 and a liquid.

20. The instant beverage according to claim 19 wherein the liquid is selected from the group consisting of water, carbonated water, and fruit juice.

21. The composition according to claim 10, wherein the composition is a gel.

22. The composition according to claim 10, wherein the composition is a sorbet.

* * * * *